United States Patent
Saito (10) Patent No.: US 11,229,415 B2
(45) Date of Patent: Jan. 25, 2022

(54) RADIOGRAPHIC IMAGING APPARATUS

(71) Applicant: Shimadzu Corporation, Kyoto (JP)

(72) Inventor: Atsuo Saito, Kyoto (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 17/017,386

(22) Filed: Sep. 10, 2020

(65) Prior Publication Data

US 2021/0137475 A1    May 13, 2021

(30) Foreign Application Priority Data

Nov. 8, 2019 (JP) .............................. JP2019-203044

(51) Int. Cl.
*A61B 6/00* (2006.01)
*A61B 6/04* (2006.01)

(52) U.S. Cl.
CPC .......... *A61B 6/4441* (2013.01); *A61B 6/0407* (2013.01); *A61B 6/4476* (2013.01); *A61B 6/487* (2013.01)

(58) Field of Classification Search
CPC ............................ A61B 6/4441; A61B 6/4476
See application file for complete search history.

(56) References Cited

U.S. PATENT DOCUMENTS

2019/0053774 A1* 2/2019 Weingarten ........ G05B 19/4061

FOREIGN PATENT DOCUMENTS

JP          2008-86836 A       4/2008
JP          2017-118910 A      7/2017

* cited by examiner

*Primary Examiner* — Dani Fox
(74) *Attorney, Agent, or Firm* — Muir Patent Law, PLLC (57) ABSTRACT

An arm moving mechanism 200 includes a first rotatable member 26 mounted on base 27 so as to be rotatable about a first rotation axis 31 perpendicular to the base 27, a second rotatable member 25 mounted on the first rotatable member 26 so as to be rotatable about a second rotation axis 32 perpendicular to the base 27, a C-shaped arm support frame 24 mounted on the second rotatable member 25 so as to be rotatable about a third rotation axis 33 perpendicular to the base 27, motors for rotating them, and a controller for controlling the motors. When the first rotatable member 26, the second rotatable member 25, and the C-shaped arm support frame 24 are moved, the radiation irradiation unit 11 and the radiation detection unit 14 are moved linearly between the imaging position for performing radiographic imaging and the retreat position retreated from the imaging position.

6 Claims, 10 Drawing Sheets

RADIOGRAPHIC IMAGING APPARATUS

CROSS-REFERENCE TO RELATED APPLICATIONS

This application claims priority under 35 U.S.C. § 119 to Japanese Patent Application No. 2019-203044 filed on Nov. 8, 2019, the entire disclosure of which is herein incorporated by reference in its entirety.

BACKGROUND OF THE INVENTION

Field of the Invention

The present invention relates to a radiographic imaging apparatus.

Description of the Prior Art

As one type of a radiographic imaging apparatus, there is an X-ray imaging apparatus for performing X-ray fluoroscopy or X-ray imaging (hereinafter collectively referred to as "X-ray imaging") when examining and operating on a cardiovascular system or the like. Such an X-ray imaging apparatus is provided with an X-ray irradiation unit equipped with an X-ray tube, an X-ray detection unit composed of an X-ray detector, such as, e.g., a flat panel detector, for detecting X-rays emitted from the X-ray irradiation unit to a subject and passed through the subject, and a generally C-shaped arm for supporting the X-ray irradiation unit and the X-ray detection unit. The C-shaped arm is allowed to slide, rotate, and move horizontally by a C-shaped arm moving mechanism. The X-rays detected by the X-ray detection unit are displayed on a display unit, such as, e.g., a liquid crystal display panel, as an X-ray fluoroscopic image of a subject.

Patent Document 1 discloses an X-ray diagnostic apparatus in which a C-shaped arm is moved using an arm moving mechanism having a two-axis link mechanism. Further, Patent Document 2 discloses a radiographic fluoroscopic imaging apparatus in which a C-shaped arm is moved in two mutually perpendicular directions along rails provided on a ceiling of an examination room.

PRIOR ART DOCUMENT

Patent Document

Patent Document 1: Japanese Unexamined Patent Application Publication No. 2008-86836
Patent Document 2: Japanese Unexamined Patent Application Publication No. 2017-118910

Problems to be Solved by the Invention

For example, when performing X-ray fluoroscopy using a catheter, surgical processing may sometimes need to be performed on the subject. In such a case, the X-ray irradiation unit and the X-ray detection unit positioned at an imaging position above and below the subject are required to retreat from the imaging position. In such a case, conventionally, the X-ray irradiation unit and the X-ray detection unit are caused to retreat from the imaging position by rotating the C-shaped arm.

Figure 9:
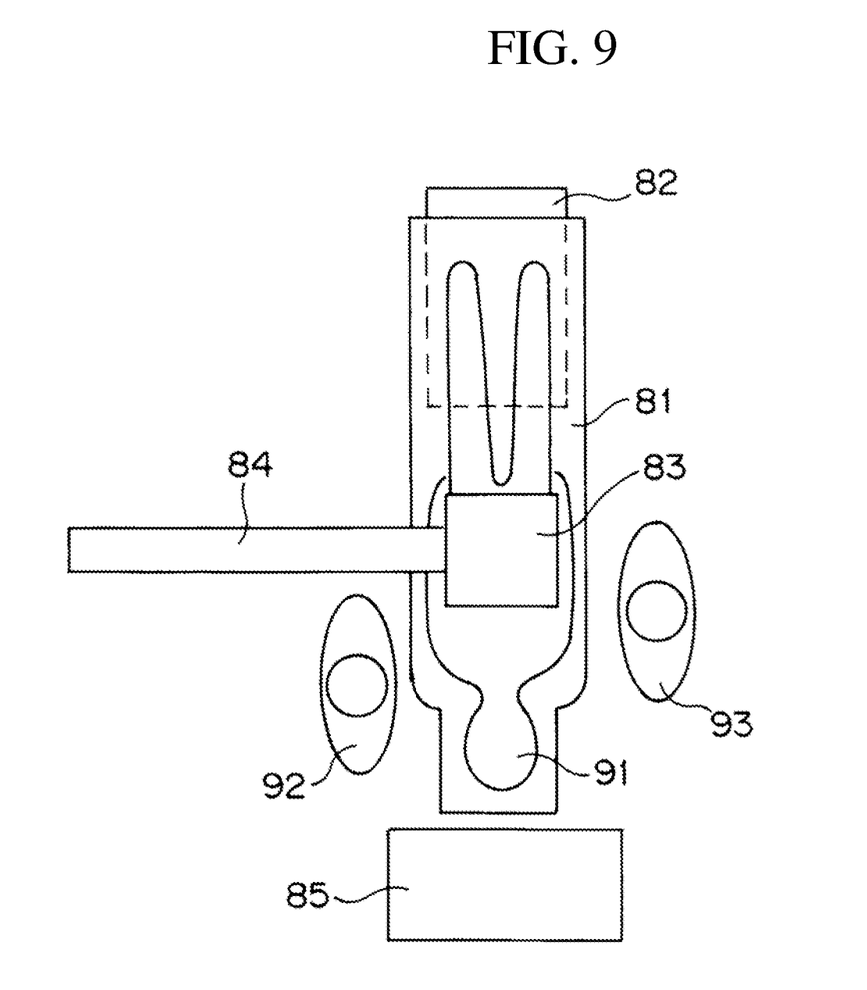
FIG. 9 is an explanatory diagram showing a retreat action in which a C-shaped arm 84 is rotated to cause an X-ray irradiation unit and an X-ray detection unit to retreat from an imaging position.
Figure 10:
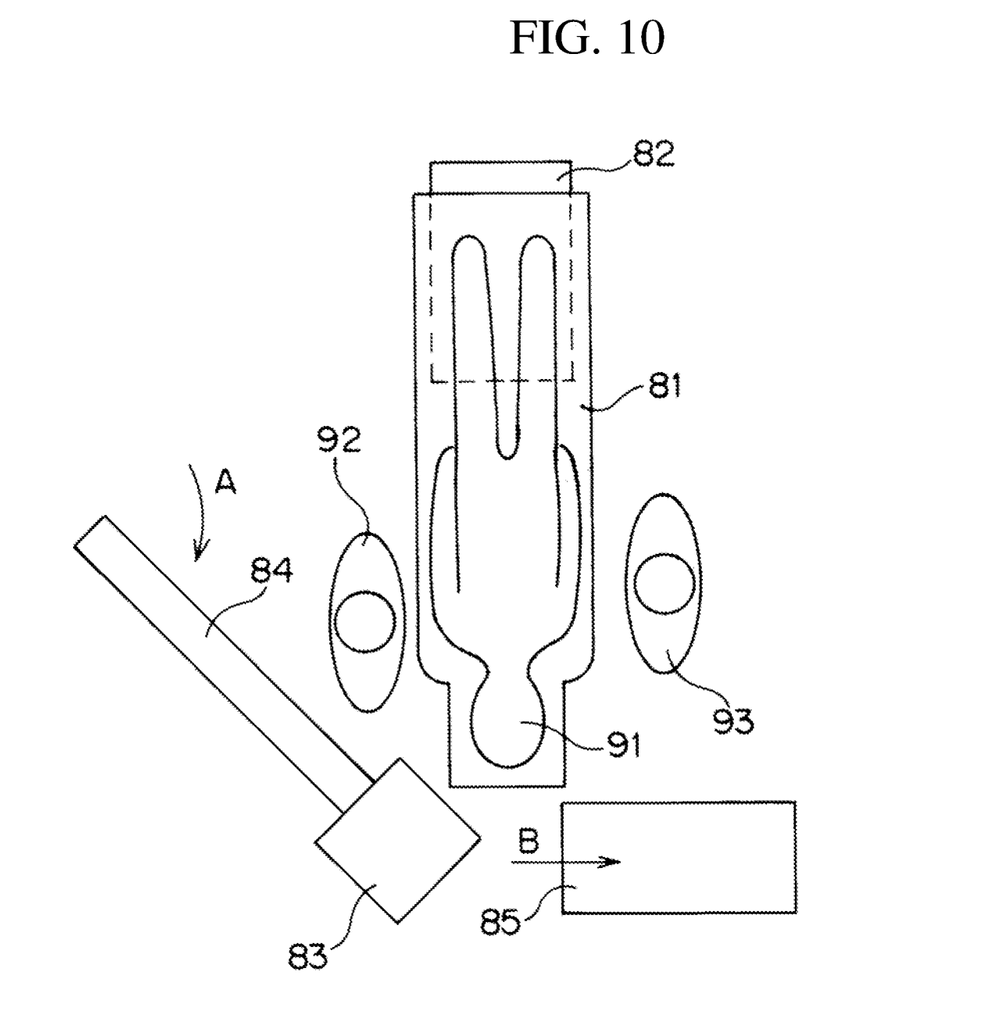
FIG. 10 is an explanatory diagram showing a retreat action in which a C-shaped arm 84 is rotated to cause an X-ray irradiation unit and an X-ray detection unit to retreat from an imaging position.

FIG. 9 and FIG. 10 are explanatory views showing a retreat action for causing an X-ray irradiation unit and an X-ray detection unit to retreat from an imaging position by rotating a C-shaped arm 84.

FIG. 9 shows a state in which X-ray fluoroscopy is being performed on a subject 91 on a top board 81 of an examination table. At this time, the X-ray irradiation unit 83 supported by the C-shaped arm 84 is arranged above the affected part of the subject 91, and the X-ray detection unit is arranged below the top board 81. Note that in some cases, the X-ray irradiation unit 83 is arranged below the top board 81 and the X-ray detection unit is arranged above the affected part of the subject 91. While X-ray fluoroscopy is being performed, a physician 92 is positioned on one side of the subject 91 and an assistant 93 is positioned on the other side of the subject. Further, a peripheral device 85, such as, e.g., a monitor and a medical device, is arranged on a head side of the subject 91. Further, a support 82 movably supporting the top board 81 is arranged below the top board 81 on the foot side of the subject 91.

In such a situation, when performing a surgical procedure or the like on the subject 91, the X-ray irradiation unit 83 may sometimes be required to retreat from the upper imaging position of the subject 91. In such a case, generally, by rotating the C-shaped arm 84, the X-ray irradiation unit 83 is caused to retreat from the upper imaging position of the subject 91. At this time, as shown in FIG. 9 and FIG. 10, the support 82 is arranged below the top board 81 on the foot side of the subject 91. For this reason, the rotation direction of the C-shaped arm 84 should be a clockwise direction as indicated by the arrow A in FIG. 10.

When the C-shaped arm 84 is rotated clockwise to cause the X-ray irradiation unit 83 to retreat from the upper imaging position of the subject 91, the physician 92 positioned on the side of the subject 91 is required to retreat once from the rotation region of the C-shaped arm 84 and then return to the side of the subject 91. Furthermore, the peripheral device 85 arranged on the head side of the subject 91 is required to be moved laterally as indicated by the arrow B in FIG. 10. For this reason, in order to cause the X-ray irradiation unit 83 to retreat from the imaging position above the subject 91, complicated operations and time are required.

As described in Patent Document 2, in cases where a configuration is adopted in which a C-shaped arm is moved in two directions perpendicular to each other along rails provided on a ceiling of an examination room, the above-described problems can be solved. However, in cases where such a configuration is adopted, not only the rails need to be provided on the ceiling of the examination room, but also the load-bearing of the ceiling needs to be increased, which requires large-scale construction work. In order to further simplify the construction work, it is conceivable to provide rails on the floor of the examination room instead of providing rails on the ceiling of the examination room. But in such cases, the rails are present on the floor, which becomes an obstacle to movements of an operator, a stretcher, or the like.

SUMMARY OF THE INVENTION

The present invention has been made to solve the above-described problems, and an object of the present invention is to provide a radiographic imaging apparatus capable of easily moving a radiation irradiation unit and a radiation detection unit between an imaging position for performing radiographic imaging and a retreat position retreated from the imaging position with a simple configuration.

Means for Solving the Problem

According to one aspect of the present invention, a radiographic imaging apparatus includes: a base; a radiation irradiation unit; a radiation detection unit; an arm configured to support the radiation irradiation unit and the radiation detection unit in a state in which the radiation irradiation unit and the radiation detection unit face with each other; and an arm moving mechanism configured to move the arm. The arm moving mechanism includes: a first rotatable member mounted on the base, the first rotatable member being rotatable about a first rotation axis perpendicular to the base; a second rotatable member mounted on the first rotatable member, the second rotatable member being rotatable about a second rotation axis perpendicular to the base; a third rotatable member mounted on the second rotatable member to support the arm, the third rotatable member being rotatable about a third rotation axis perpendicular to the base; and a rotatable member rotation mechanism configured to rotate the first rotatable member, the second rotatable member, and the third rotatable member. The radiographic imaging apparatus further includes a rotation controller configured to control the rotatable member rotation mechanism so that the radiation irradiation unit and the radiation detection unit are moved linearly between an imaging position for performing radiographic imaging is performed and a retreat position retreated from the imaging position.

According to the radiographic imaging apparatus according to the above-described aspect of the present invention, it is possible to move the radiation irradiation unit and the radiation detection unit linearly between the imaging position for performing radiographic imaging and the retreat position retreated from the imaging position with a simple configuration.

EMBODIMENTS FOR CARRYING OUT THE INVENTION

Figure 1:
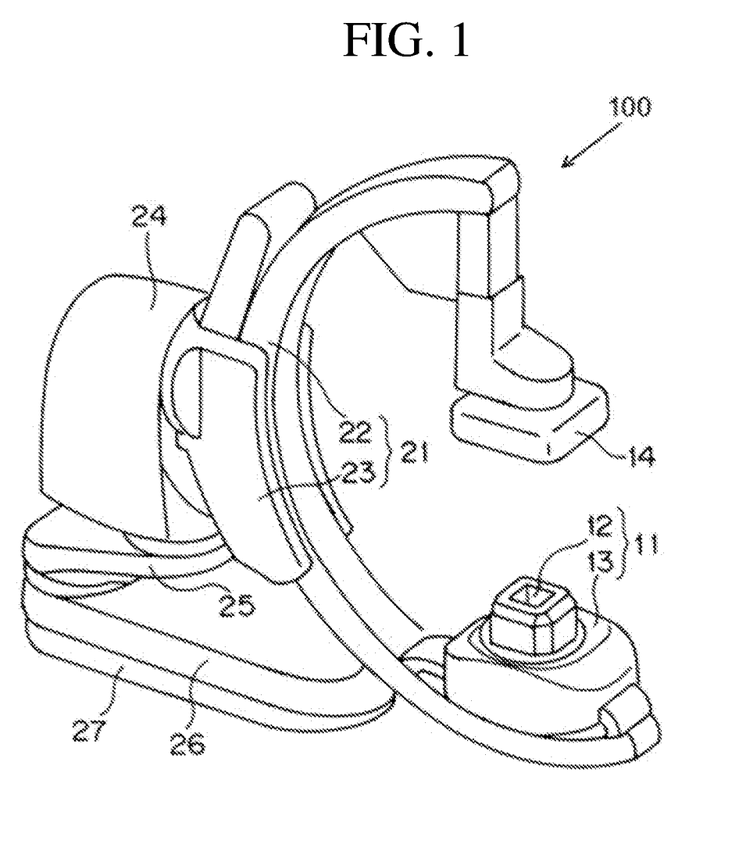
FIG. 1 is a perspective view of an X-ray imaging apparatus 100 as a radiographic imaging apparatus according to one embodiment of the present invention.
Figure 2A:
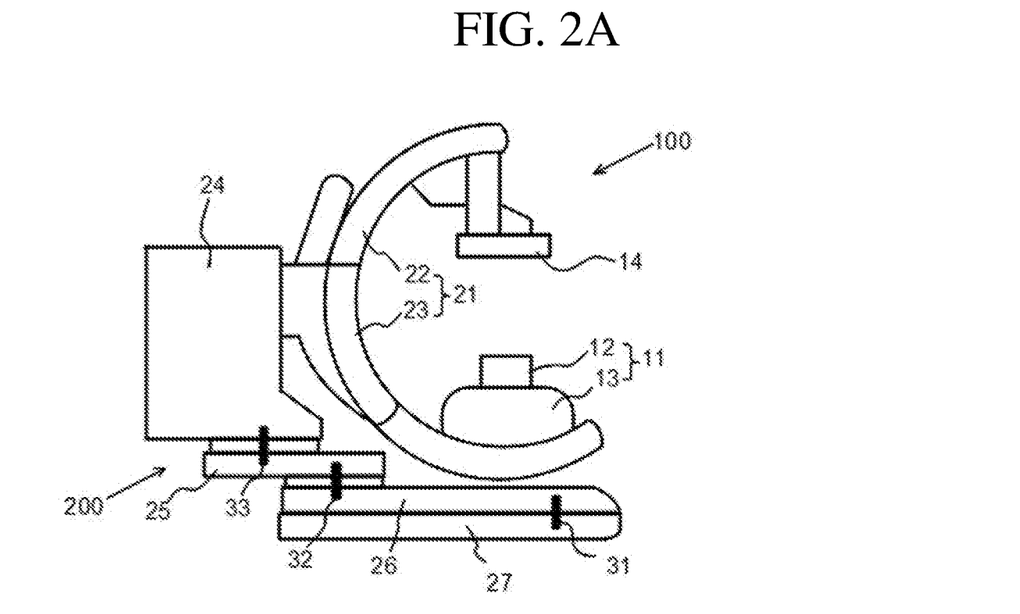
FIG. 2A is a schematic side view of the X-ray imaging apparatus 100.
Figure 2B:
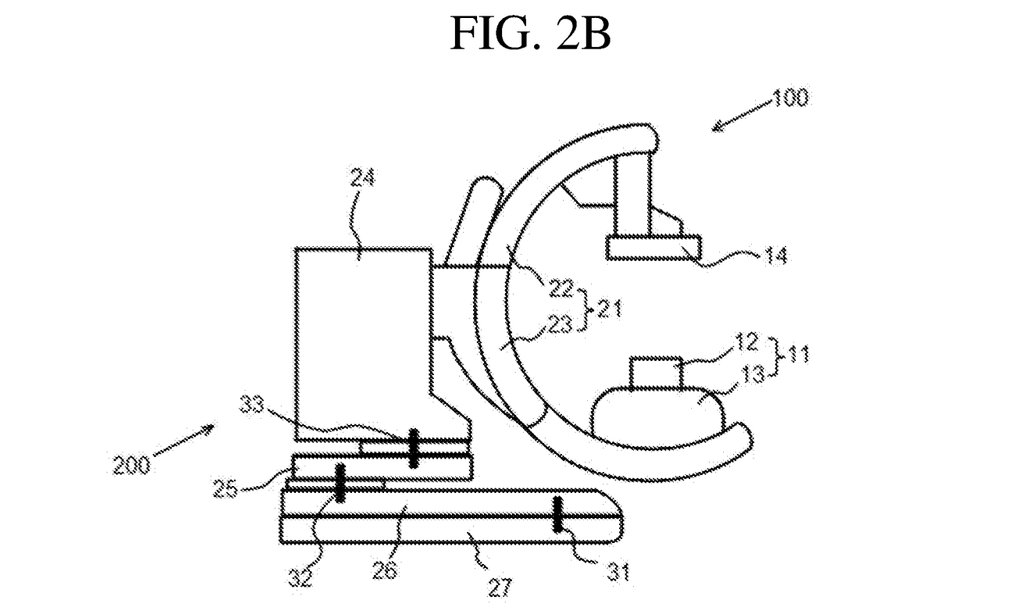
FIG. 2B is a schematic side view of the X-ray imaging apparatus 100.

Hereinafter, an embodiment of the present invention will be described with reference to the attached drawings. FIG. 1 is a perspective view of an X-ray imaging apparatus 100 as a radiographic imaging apparatus according to this embodiment. FIG. 2A and FIG. 2B are schematic side views each showing the configuration of the X-ray imaging apparatus 100.

The X-ray imaging apparatus 100 is provided with an X-ray irradiation unit 11 equipped with an X-ray tube 13 and a collimator 12, an X-ray detection unit 14 composed of a flat panel detector, a C-shaped arm 21 supporting the X-ray irradiation unit 11 and the X-ray detection unit 14 in a state in which the X-ray irradiation unit 11 and the X-ray detection unit 14 face with each other, and an arm moving mechanism 200 for moving the C-shaped arm 21. The C-shaped arm 21 is composed of an arm body 22 and a slide support 23 slidably supporting the arm body 22.

Further, the X-ray imaging apparatus 100 is provided with a base 27, a first rotatable member 26 mounted on the base 27 and configured to be rotatable about a first rotation axis 31 perpendicular to the base 27, a second rotatable member 25 mounted on the first rotatable member 26 and configured to be rotatable about a second rotation axis 32 perpendicular to the base 27, and a C-shaped arm support frame 24 mounted on the second rotatable member 25 and configured to be rotatable about a third rotation axis 33 perpendicular to the base 27. The slide support 23 is supported by the C-shaped arm support frame 24 so as to be rotatable about a rotation axis parallel to the base 27. Note that the C-shaped arm support frame 24 functions as the third rotatable member according to the present invention.

The base 27 is fixed to a floor of a room where the X-ray imaging apparatus 100 is installed. When the floor is a horizontal plane, the first rotation axis 31, the second rotation axis 32, and the third rotation axis 33 are all orientated in the vertical direction, and the rotation axis of the slide support 23 is orientated in the horizontal direction.

The first rotatable member 26, the second rotatable member 25, and the C-shaped arm support frame 24 and the C-shaped arm 21 coupled with each other constitute a three-axis link mechanism in which each of them functions as a link. Depending on the relative positional relationship between the first to third rotation axes 31 to 33, for example, as shown in FIG. 2A and FIG. 2B, the relative position of the X-ray irradiation unit 11 and the X-ray detection unit 14 with respect to the base 27 is determined. The first rotatable member 26, the second rotatable member 25, and the C-shaped arm support frame 24 and the C-shaped arm 21 are each set to a length having a predetermined relation to each other. As a result, as will be described later, the X-ray irradiation unit 11 and the X-ray detection unit 14 are configured to be linearly movable between the imaging position for performing X-ray imaging and the retreat position retreated from the imaging position by the three-axis link mechanism.

Figure 3:
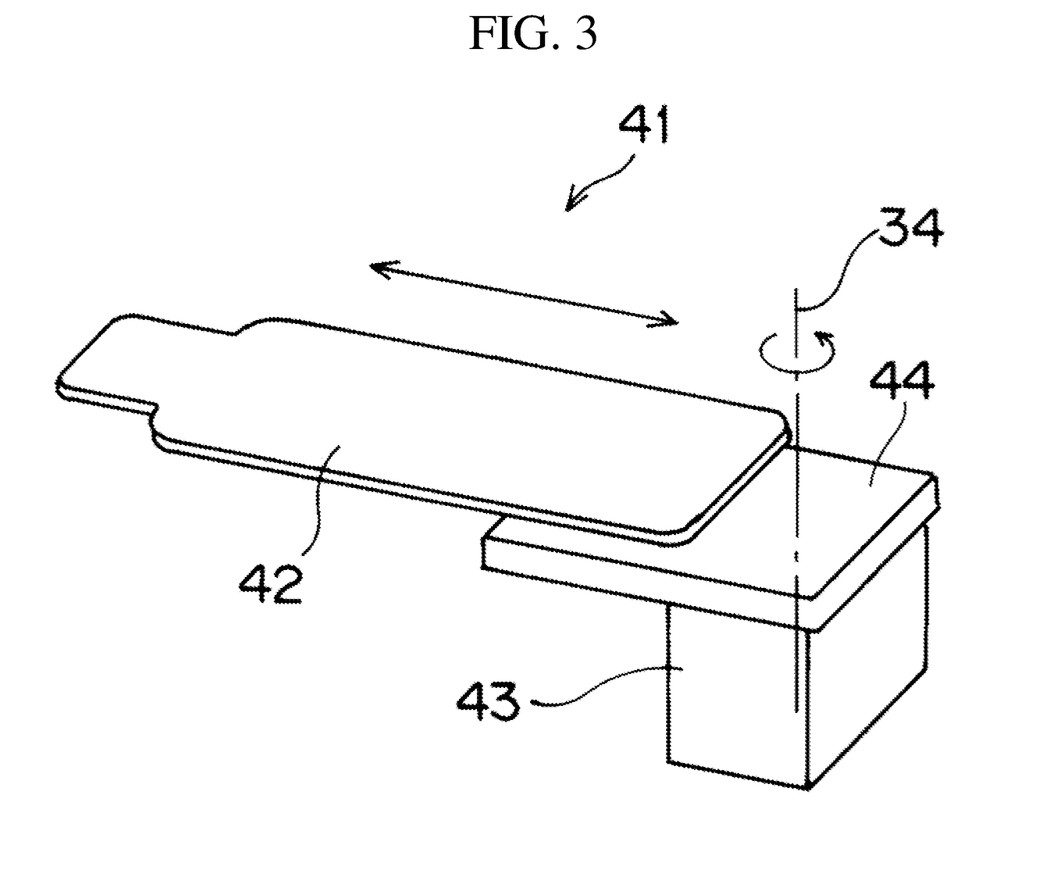
FIG. 3 is a perspective view of an examination table 41.

FIG. 3 is a perspective view of an examination table 41 constituting the X-ray imaging apparatus 100.

This examination table 41 is provided with a base 43 fixed to the floor of the room, a support 44 mounted on the base 43 and configured to be rotatable about a fourth rotation axis 34 perpendicular to the base 43, and a top board 42 movable in the arrow direction shown in FIG. 3 with respect to the support 44. The top board 42 functions as a subject placement portion for placing a subject thereon. The top board 42 is composed of an elongated plate-like member with one end narrower than the other. A head of a subject is placed on the narrow part. The top board 42 rotates together with the support 44 about the fourth rotation axis 34. When the floor of the room is a horizontal plane, the fourth rotation axis 34 is orientated in the vertical direction. Further, the top board 42 moves in the horizontal direction.

Figure 4:
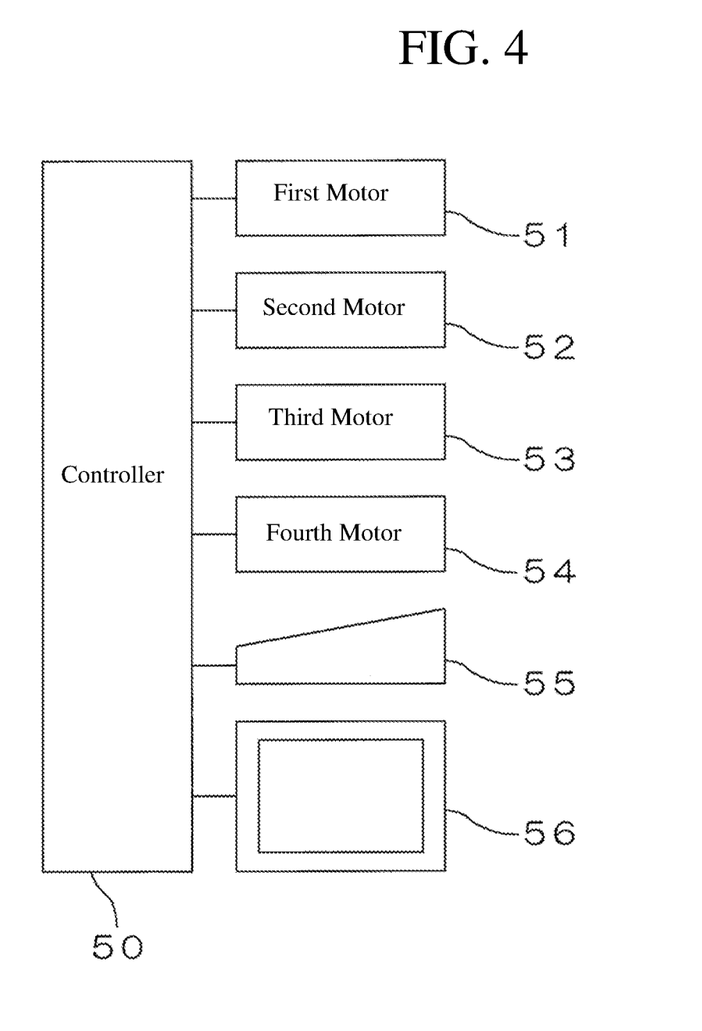
FIG. 4 is a block diagram showing a major control system for moving a C-shaped arm 21 and a top board 42.

FIG. 4 is a block diagram showing a major control system for moving the C-shaped arm 21 and the top board 42.

The X-ray imaging apparatus 100 is provided with a controller 50 for controlling the entire apparatus. The X-ray imaging apparatus 100 is provided with a first motor 51 for rotating the first rotatable member 26 about the first rotation axis 31, a second motor 52 for rotating the second rotatable member 25 about the second rotation axis 32, a third motor 53 for rotating the C-shaped arm support frame 24 and the C-shaped arm 21 about the third rotation axis 33, and a fourth motor 54 for rotating the top board 42 together with the support 44 about the fourth rotation axis 34. Note that the first motor 51, the second motor 52, the third motor 53 correspond to the rotatable member rotation mechanism of the present invention, and the fourth motor 54 corresponds to the placement portion rotation mechanism of the present invention. The controller 50 is connected to the first motor 51, the second motor 52, the third motor 53, and the fourth motor 54.

Further, the controller 50 is connected to an operation unit 55 equipped with a mouse and a keyboard and a display unit 56 composed of, e.g., a liquid crystal display. The operation unit 55 functions, as described later, as an input unit for inputting a movement destination when moving the X-ray irradiation unit 11 and the X-ray detection unit 14 via the first rotatable member 26, the second rotatable member 25, and the C-shaped arm support frame 24 and the C-shaped arm 21 coupled to each other. Further, the operation unit 55 functions as an input unit for inputting a movement amount when moving the top board 42 of the examination table 41.

The controller 50 realizes its function according to software installed on a computer including a CPU, etc., as a hardware resource.

Next, in the X-ray imaging apparatus 100, the operation of moving the X-ray irradiation unit 11 and the X-ray detection unit 14 between the imaging position and the retreat position will be described with reference to FIG. 5 to FIG. 8.

Figure 5:
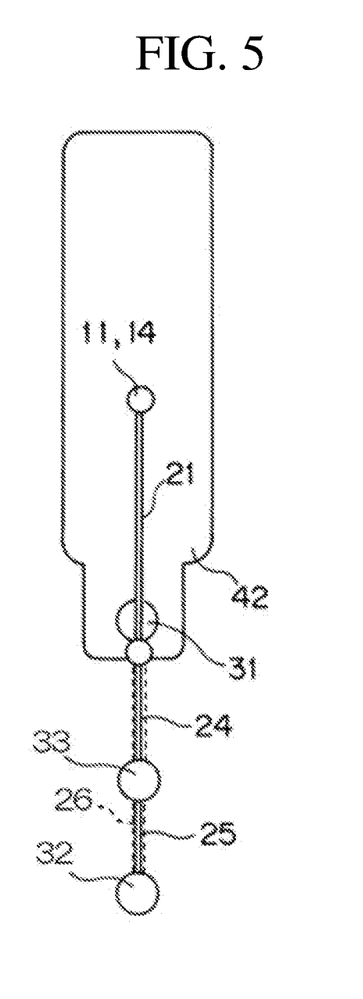
FIG. 5 is an explanatory diagram schematically showing a state in which an X-ray irradiation unit 11 and an X-ray detection unit 14 are moved between the imaging position and the retreat position.
Figure 6:
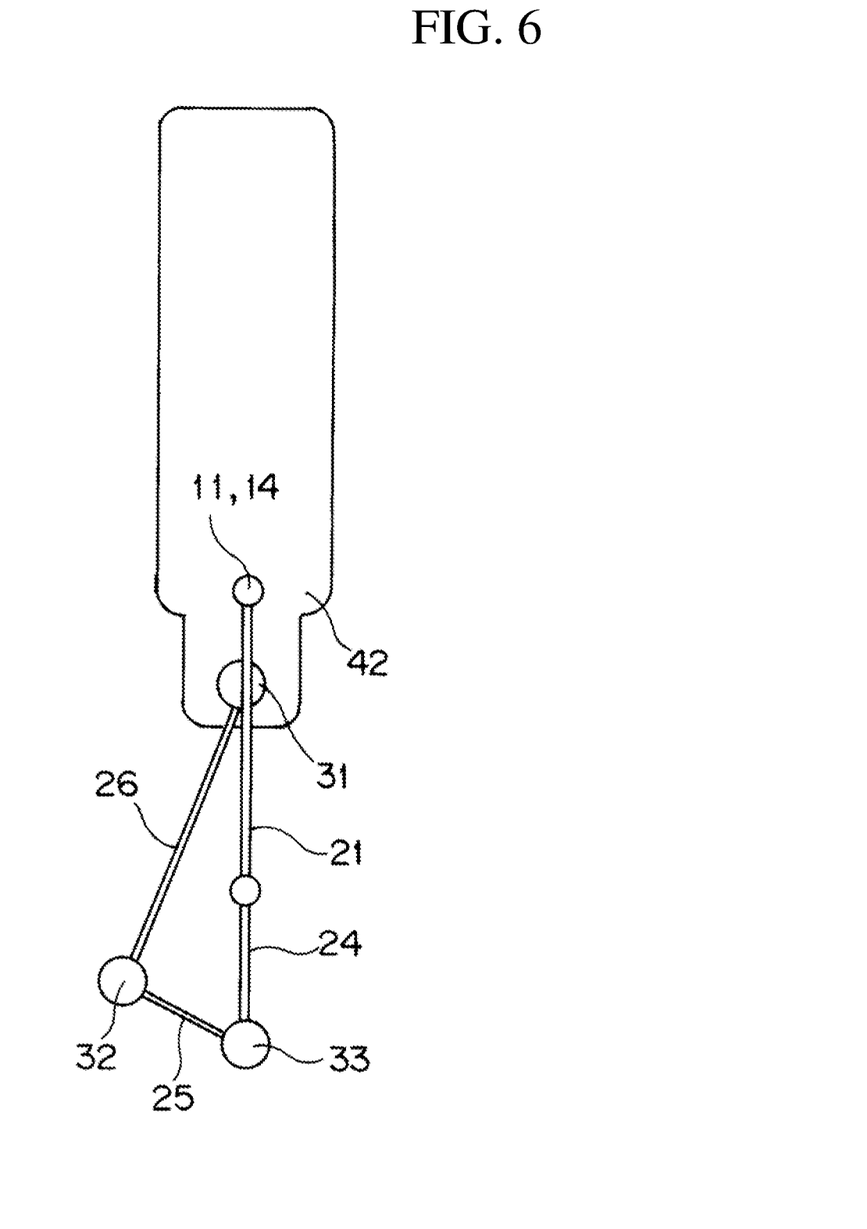
FIG. 6 is an explanatory diagram schematically showing a state in which the X-ray irradiation unit 11 and the X-ray detection unit 14 are moved between the imaging position and the retreat position.

FIG. 5 and FIG. 6 are schematic diagrams for explaining the operation of moving the X-ray irradiation unit 11 and the X-ray detection unit 14 between the imaging position and the retreat position from the head side of the subject. When moving the X-ray irradiation unit 11 and the X-ray detection unit 14 from the head side of the subject, as shown in FIG. 5, the first rotatable member 26, the second rotatable member 25, and the C-shaped arm support frame 24 and the C-shaped arm 21, which constitute a three-axis link mechanism, are arranged on the same straight line along the longitudinal direction of the top board 42 of the examination table 41 (the body axis direction of the subject placed on the top board). At this time, the first rotatable member 26, the second rotatable member 25, the C-shaped arm support frame 24 and the C-shaped arm 21 cross the center of the top board 42 in the short direction thereof, and the X-ray irradiation unit 11 and the X-ray detection unit 14 are arranged at the imaging position facing with each other via the affected portion of the subject.

FIG. 5 shows a state in which the third rotation axis 33 is positioned on the top board 42 side than the second rotation axis 32 (see FIG. 2B). When the affected position (imaging position) of the subject is on the foot side or the head side of the subject than the position shown in FIG. 5, the angle of the first rotatable member 26 and the angle of the second rotatable member 25 with respect to the C-shaped arm support frame 24 and the C-shaped arm 21 may be changed while maintaining the orientation of the C-shaped arm support frame 24 and the C-shaped arm 21. Further, the second rotation axis 32 may be arranged on the top board 42 side than the third rotation axis 33 (see FIG. 2A). Further, the top board 42 of the examination table 41 may be moved in the body axis direction of the subject.

On the other hand, when moving the X-ray irradiation unit 11 and the X-ray detection unit 14 arranged at the imaging position shown in FIG. 5 to a retreat position, the first rotatable member 26 is rotated clockwise about the first rotation axis 31. Further, the second rotatable member 25 is rotated clockwise about the second rotation axis 32, and the C-shaped arm support frame 24 and C-shaped arm 21 are rotated counterclockwise about the third rotation axis 33.

With this, as shown in FIG. 6, the X-ray irradiation unit 11 and the X-ray detection unit 14 are moved to the retreat position retreated to the head side of the subject than the imaging position shown in FIG. 5. At this time, the controller 50 is configured to control the respective rotational amounts and rotational speeds of the first motor 51, the second motor 52, and the third motor 53 to thereby linearly move the X-ray irradiation unit 11 and the X-ray detection unit 14 from the imaging position to the retreat position. That is, in this embodiment, the controller 50 functions as a rotation controller. Therefore, even when the X-ray irradiation unit 11 and the X-ray detection unit 14 are caused to temporarily retreat from the imaging position in order to perform a surgical procedure or the like on the subject when X-ray imaging is being performed with the X-ray irradiation unit 11 and the X-ray detection unit 14 arranged at the facing position via the affected part of the subject, the retreat action of the physician 92 and the moving operation of the peripheral device 85 are not required.

When returning the X-ray irradiation unit 11 and the X-ray detection unit 14 from the retreat position to the imaging position, the first rotatable member 26 is rotated counterclockwise about the first rotation axis 31, and the second rotatable member 25 is rotated counterclockwise about the second rotation axis 32. Further, the C-shaped arm support frame 24 and the C-shaped arm 21 are rotated clockwise about the third rotation axis 33. With this, the X-ray irradiation unit 11 and the X-ray detection unit 14 can be linearly moved from the retreat position shown in FIG. 6 to the imaging position shown in FIG. 5.

Figure 7:
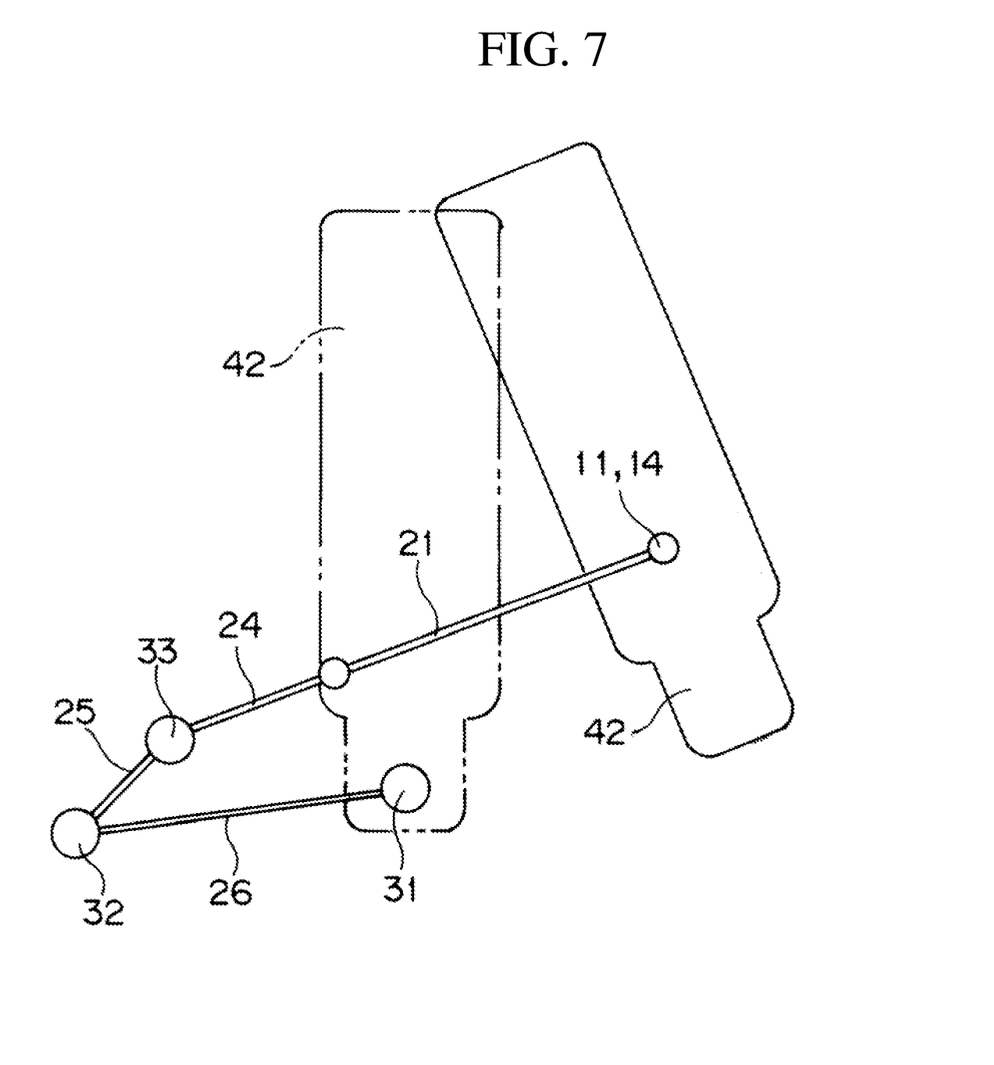
FIG. 7 is an explanatory diagram schematically showing a state in which the X-ray irradiation unit 11 and the X-ray detection unit 14 are moved between the imaging position and the retreat position.

Next, the operation of moving the X-ray irradiation unit 11 and the X-ray detection unit 14 from the side of the subject between the imaging position and the retreat position. In this case, as shown in FIG. 7, the first rotatable member 26, the second rotatable member 25, and the C-shaped arm support frame 24 and the C-shaped arm 21 coupled to each other, which constitute a three-axis link mechanism, are rotated about the respective first rotation axis 31, second rotation axis 32, and third rotation axis 33. Further, the top board 42 of the examination table 41 is rotated together with the support 44 about the fourth rotation axis 34 from the position shown by the imaginary line in FIG. 7 to the position shown by the solid line. With this, the X-ray irradiation unit 11 and the X-ray detection unit 14 are arranged at the imaging position facing each other across the affected portion of the subject, and the C-shaped arm support frame 24 and the C-shaped arm 21 are orientated in the lateral direction of the top board 42 (the direction perpendicular to the body axis of the subject).

When temporality causing the X-ray irradiation unit 11 and the X-ray detection unit 14 in the imaging position shown in FIG. 7 to retreat, the first rotatable member 26 is rotated counterclockwise about the first rotation axis 31, and the second rotatable member 25 is rotated counterclockwise about the second rotation axis 32. Further, the C-shaped arm support frame 24 and the C-shaped arm 21 are rotated clockwise about the third rotation axis 33.

Figure 8:
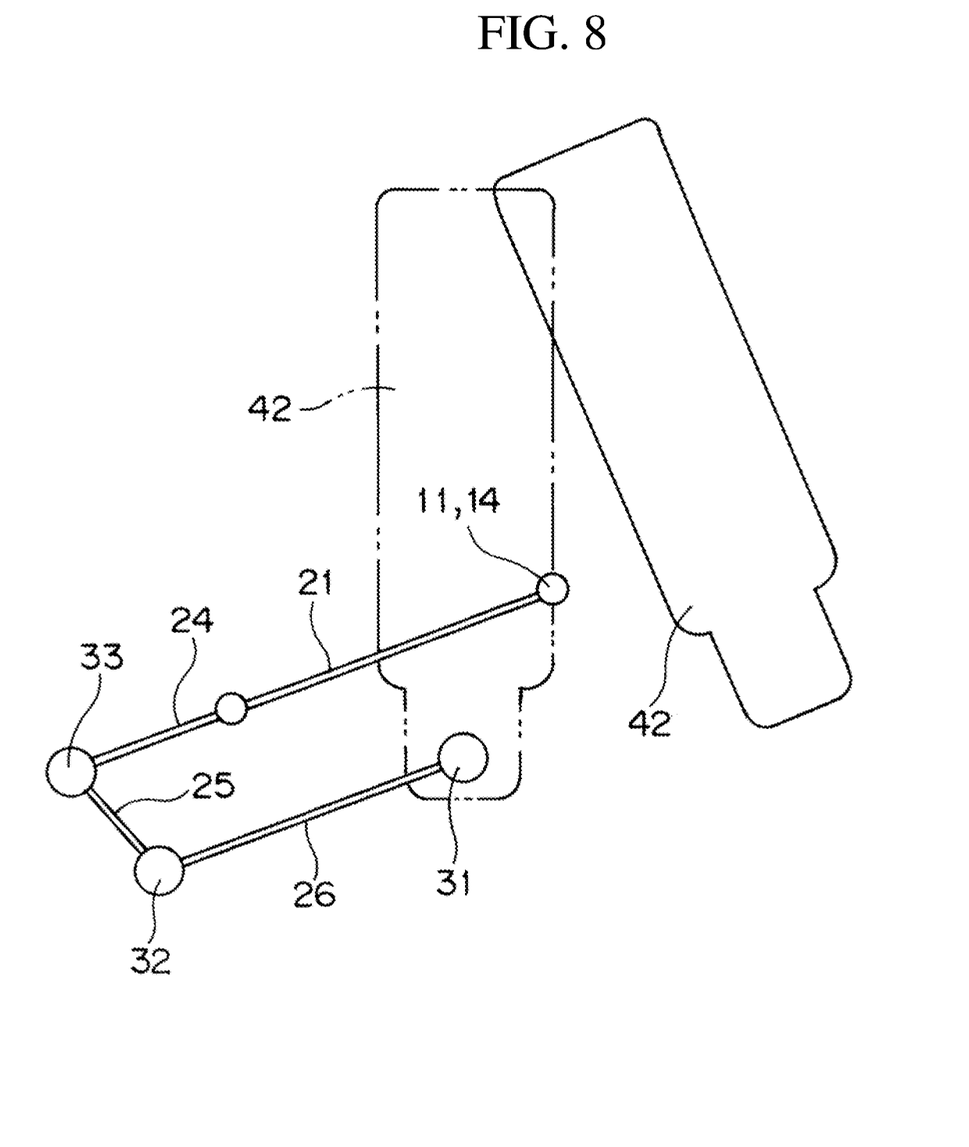
FIG. 8 is an explanatory view schematically showing a state in which the X-ray irradiation unit 11 and the X-ray detection unit 14 are moved between the imaging position and the retreat position.

Thus, as shown in FIG. 8, it is possible to move the X-ray irradiation unit 11 and the X-ray detection unit 14 present at the imaging position to the retreat position retreated to the side of the top board 42. At this time, the controller 50 controls the respective rotational amounts and rotational speeds of the first motor 51, the second motor 52, and the third motor 53, so that the X-ray irradiation unit 11 and the X-ray detection unit 14 can be linearly moved from the imaging position toward the retreat position. That is, in this embodiment, the controller 50 functions as a second rotation controller. Also in this case, the retreat action of the physician 92 and the moving operation of the peripheral device 85 are not required.

When causing the X-ray irradiation unit 11 and the X-ray detection unit 14 to return from the retreat position to the imaging position, the first rotatable member 26 is rotated clockwise about the first rotation axis 31, the second rotatable member 25 is rotated clockwise about the second rotation axis 32, and further, the C-shaped arm support frame 24 and the C-shaped arm 21 are rotated counterclockwise about the third rotation axis 33. With this, the X-ray irradiation unit 11 and the X-ray detection unit 14 can be linearly moved from the retreat position shown in FIG. 8 to the imaging position shown in FIG. 7.

As described above, according to the X-ray imaging apparatus 100 of this embodiment, since the first rotatable member 26, the second rotatable member 25, the C-shaped arm support frame 24 and the C-shaped arm 21 each having a predetermined relation in length constitute a three-axis link mechanism and that the first rotatable member 26, the second rotatable member 25, and the C-shaped arm support frame 24 and the C-shaped arm 21 are rotated at predetermined speed, respectively, it is possible to linearly move the X-ray irradiation unit 11 and the X-ray detection unit 14 between the imaging position and the retreat position retreated from the imaging position.

It should be appreciated by those skilled in the art that the above-described exemplary embodiment is illustrative of the following aspects.

(Item 1)

According to one aspect of the present invention, a radiographic imaging apparatus comprising:

a base;

a radiation irradiation unit;

a radiation detection unit;

an arm configured to support the radiation irradiation unit and the radiation detection unit in a state in which the radiation irradiation unit and the radiation detection unit face with each other; and an arm moving mechanism configured to move the arm, wherein the arm moving mechanism includes:

a first rotatable member mounted on the base, the first rotatable member being rotatable about a first rotation axis perpendicular to the base;

a second rotatable member mounted on the first rotatable member, the second rotatable member being rotatable about a second rotation axis perpendicular to the base;

a third rotatable member mounted on the second rotatable member to support the arm, the third rotatable member being rotatable about a third rotation axis perpendicular to the base; and a rotatable member rotation mechanism configured to rotate the first rotatable member, the second rotatable member, and the third rotatable member, and wherein the radiographic imaging apparatus further comprises a rotation controller configured to control the rotatable member rotation mechanism so that the radiation irradiation unit and the radiation detection unit are moved linearly between an imaging position for performing radiographic imaging and a retreat position retreated from the imaging position.

According to the radiographic imaging apparatus described in the above-described Item 1, although the configuration is simple, it is possible to linearly move the radiation irradiation unit and the radiation detection unit between the imaging position for performing radiographic imaging and the retreat position.

(Item 2)

The radiographic imaging apparatus as recited in the above-described Item 1, further including:

an examination table including a subject placement portion for placing a subject thereon and a placement portion rotation mechanism for rotating the subject placement portion about a fourth rotation axis perpendicular to the base; and a second rotation controller configured to control the rotatable member rotation mechanism and the placement portion rotation mechanism so that the radiation irradiation unit and the radiation detection unit are moved between the imaging position and the retreat position along a body axis of the subject placed on the subject placement portion.

According to the radiographic imaging apparatus of the above-described Item 2, the radiation irradiation unit and the radiation detection unit can be linearly moved along the body axis of the subject placed on the subject placement portion by moving the arm by the rotatable member rotation mechanism and rotating the subject placement portion by the placement portion rotation mechanism.

(Item 3)

The radiographic imaging apparatus as recited in the above-described Item 1, further including:

an examination table including a subject placement portion for placing a subject thereon and a placement portion rotation mechanism for rotating the subject placement portion about a fourth rotation axis perpendicular to the base; and a second rotation controller configured to control the rotatable member rotation mechanism and the placement portion rotation mechanism so that the radiation irradiation unit and the radiation detection unit are moved between the imaging position and the retreat position in a direction intersecting with a body axis of the subject placed on the subject placement portion.

According to the radiographic imaging apparatus of the above-described Item 3, the radiation irradiation unit and the radiation detection unit can be linearly moved in the direction intersecting with the body axis of the subject placed on the subject placement portion by moving the arm by the rotatable member rotation mechanism and rotating the subject placement portion by the placement portion rotation mechanism.

(Item 4)

The radiographic imaging apparatus as recited in the above-described Item 1, wherein the base is fixed to a horizontal plane.

According to the radiographic imaging apparatus as described in the above-described Item 4, with a simple configuration in which the base is fixed to the horizontal plane, all of the first to third rotation axes are orientated in the vertical direction, which makes it possible to linearly move the radiation irradiation unit and the radiation detection unit between the imaging position for performing radiographic imaging and the retreat position retreated from the imaging position.

It should be noted that the above-described description is for the purpose of explaining the embodiments of the present invention and is not intended to limit the present invention.

DESCRIPTION OF SYMBOLS

11: X-ray irradiation unit
12: Collimator
13: X-ray tube
14: X-ray detection unit
21: C-shaped arm
24: C-shaped arm support frame
25: Second rotatable member
26: First rotatable member
27: Base
31: First rotation axis
32: Second rotation axis
33: Third rotation axis
34: Fourth rotation axis
41: Examination table
42: Top board
44: Support table
50: Controller
51: First motor
52: Second motor
53: Third motor
54: Fourth motor
55: Operation unit

The invention claimed is:

1. A radiographic imaging apparatus comprising:
a base;
a radiation irradiation unit;
a radiation detection unit;
an arm configured to support the radiation irradiation unit and the radiation detection unit in a state in which the radiation irradiation unit and the radiation detection unit face with each other; and
an arm moving mechanism configured to move the arm, wherein the arm moving mechanism includes:
a first rotatable member mounted on the base, the first rotatable member being rotatable about a first rotation axis perpendicular to the base;
a second rotatable member mounted on the first rotatable member, the second rotatable member being rotatable about a second rotation axis perpendicular to the base;
a third rotatable member mounted on the second rotatable member to support the arm, the third rotatable member being rotatable about a third rotation axis perpendicular to the base; and
a rotatable member rotation mechanism configured to rotate the first rotatable member, the second rotatable member, and the third rotatable member, and
wherein the radiographic imaging apparatus further comprises a rotation controller configured to control the rotatable member rotation mechanism so that the radiation irradiation unit and the radiation detection unit are moved linearly between an imaging position for performing radiographic imaging and a retreat position retreated from the imaging position.

2. The radiographic imaging apparatus as recited in claim 1, further comprising:
an examination table including a subject placement portion for placing a subject thereon and a placement portion rotation mechanism for rotating the subject placement portion about a fourth rotation axis perpendicular to the base; and
a second rotation controller configured to control the rotatable member rotation mechanism and the placement portion rotation mechanism so that the radiation irradiation unit and the radiation detection unit are moved between the imaging position and the retreat position along a body axis of the subject placed on the subject placement portion.

3. The radiographic imaging apparatus as recited in claim 1, further comprising:
an examination table including a subject placement portion for placing a subject thereon and a placement portion rotation mechanism for rotating the subject placement portion about a fourth rotation axis perpendicular to the base; and
a second rotation controller configured to control the rotatable member rotation mechanism and the placement portion rotation mechanism so that the radiation irradiation unit and the radiation detection unit are moved between the imaging position and the retreat position in a direction intersecting with a body axis of the subject placed on the subject placement portion.

4. The radiographic imaging apparatus as recited in claim 1, wherein the base is fixed to a horizontal plane.

5. The radiographic imaging apparatus as recited in claim 2, wherein the base is fixed to a horizontal plane.

6. The radiographic imaging apparatus as recited in claim 3, wherein the base is fixed to a horizontal plane.

* * * * *